United States Patent [19]
Schatzberg et al.

[11] Patent Number: 6,150,349
[45] Date of Patent: Nov. 21, 2000

[54] METHODS FOR TREATING PSYCHOSIS ASSOCIATED WITH GLUCOCORTICOID RELATED DYSFUNCTION

[75] Inventors: Alan F. Schatzberg, Los Altos; Joseph K. Belanoff, Cupertino, both of Calif.

[73] Assignee: The Board of Trustees of the Leland Stanford Junior University, Palo Alto, Calif.

[21] Appl. No.: 09/244,457

[22] Filed: Feb. 4, 1999

Related U.S. Application Data

[63] Continuation of application No. PCT/US98/20906, Oct. 5, 1998.
[60] Provisional application No. 60/060,973, Oct. 6, 1997.
[51] Int. Cl.$^7$ .................................................. A61K 31/56
[52] U.S. Cl. ............................................................ 514/179
[58] Field of Search ............................................. 514/179

[56] References Cited

U.S. PATENT DOCUMENTS 4,814,333   3/1989   Ravaris ................................... 514/255

FOREIGN PATENT DOCUMENTS

| 0763541 | 3/1997 | European Pat. Off. . |
|---|---|---|
| WO 9322685 | 11/1993 | WIPO . |
| WO 9408588 | 4/1994 | WIPO . |
| WO 9710827 | 3/1997 | WIPO . |
| WO 9737664 | 10/1997 | WIPO . |
| WO 9826783 | 6/1998 | WIPO . |
| WO 9826785 | 6/1998 | WIPO . |

OTHER PUBLICATIONS

Van der Lely, Derwent Drug File, abstract No. 1993–29824, 1993.
Piazza et al, Chemical Abstracts, abstract No. 126:84476, 1996.
Behl et al, Chemical Abstracts, abstract No. 126:55042, 1997.
Beck C.A. et al. (1993) "The Steroid Antagonist RU486 Exerts Different Effects on the Glucocorticoid and Progesterone Receptors" Department of Pathology and Program in Molecular Biology, University of Colorado Health Sciences Center (S.K.N.D.P.E.) vol. 123, No. 2, pp. 728–740.
Chrousos, G.P. et al. (1989) "Clinical Applications of RU 486, a Prototype Glucocorticoid and Progestin Antagonist." In:Baulieu, E.E. and Segal, S.J. eds. The Antiprogestin Steroid RU 486 and Human Fertility Control. New York: Plenum Press, pp. 273–284.

F. Cadepond, Ph.D. et al., (1997) "RU486 (Mifepristone): Mechanisms of Action and Clinical Uses" Anna. Rev. Med. 1997, 48:129–56.
Krishnan, K.R.R.et al. (1992) "RU 486 in depression" Prog. Neuro–Psychopharmacol. & Biol. Psychiat., 16:913–920.
Murphy, B.E.P. et al. (1993) "Possible Use of Glucocorticoid Receptor Antagonists in the Treatment of Major Depression: Preliminary Results Using RU 486" J. Psychiatr. Neurosci., 18:209–213.
Murphy, B.E.P. s(1997) "Antiglucocorticoid therapies in major depression: A review" Psychoneuroendocrinology, 22:s125–132.
Nieman, L.K. et al. (1985) "Successful treatment of Cushing's Syndrome with the Glucocorticoid Antagonist RU 486" J. Clin. Endocrinol. Metab., 61:536–540.
Rothschild, A.J. et al. (1982) "The Dexamethasone Suppression Test as a Discriminator among Subtypes of Psychotic Patients" Brit. J. Psychiat. 141:471–474.
Rothschild, A.J. et al. (1985) "The effects of a single acute dose of dexamethasone on monoamine and metabolite levels in rat brain" Life Sci. 36:2491–2501.
Sartor, O.et al. (1996) "Mifepristone: Treatment of Cushing's Syndrome" Clin. Obstetrics and Gynecol. 39:506–510.
Schatzberg, A.F. et al. (1983) "The Dexamathasone Suppression Test: Identification of Subtypes of Depression" Am. J. Psychiat., 140:88–91.
Schatzberg, A.F. et al. (1985) "A corticosteriod/dopamine hypothesis for psychotic depression and related states" J. Psychiat. Res., 19:57–64.
Schatzberg, A.F. et al. (1988) "The Roles of Glucocorticoid and Dopaminergic Systems in Delusional (Psychotic) Depression" Annals N.Y. Acad. of Sci., 537:462–471.
Van der Lely, A.J. et al. (1991) "Rapid Reversal of Acute Psychosis in the Cushing Syndrome with the Cortisol–Receptor Antagonist Mifepristone (RU 486)" Ann. Intern. Med., 114:143–144.
Van der Lely, A.J. (1993) Pharmacy World & Science, 15:89–90.

*Primary Examiner*—William R. A. Jarvis
*Attorney, Agent, or Firm*—Bozicevic, Field & Francis

[57] ABSTRACT

This invention pertains to the discovery that agents which inhibit the binding of cortisol to its receptors can be used in methods for amelirating psychotic major depression. Mifepristone, a potent glucocorticoid receptor antagonist, can be used in these methods.

13 Claims, No Drawings

METHODS FOR TREATING PSYCHOSIS ASSOCIATED WITH GLUCOCORTICOID RELATED DYSFUNCTION

CROSS REFERENCE TO RELATED APPLICATIONS

The present application is a continuation of PCT/US98/20906, filed Oct 5, 1998 which is a Continuation-In-Part application of U.S. Provisional Application Ser. No. 60/060,973, filed Oct. 06, 1997. The aforementioned application is explicitly incorporated herein by reference in its entirety and for all purposes.

FIELD OF THE INVENTION

This invention generally pertains to the field of psychiatry. In particular, this invention pertains to the discovery that agents which inhibit the binding of cortisol to its receptor can be used in methods of ameliorating psychosis, including the psychotic component of pathologies or conditions with psychotic symptoms.

INTRODUCTION

This invention is directed to a method for treating psychosis whose pathogenesis is related to glucocorticoid regulatory dysfunction. The types of psychosis treated by the methods of the invention must be distinguished from the older definition of psychosis, which referred to schizophrenia and manic states. Schizophrenia and manic states are not associated with dysfunction of the glucocorticoid regulatory pathway and there is no basis to believe that possibility. Thus, the treatment methods of the invention encompass the modem usage of the term psychosis, i.e., non-schizophrenia and non-manic state associated psychosis.

There has been historic confusion in the definition of psychosis. This is, in part, based on a lack of understanding of a common pathophysiologic mechanism causing psychosis in various conditions. For example, Oberlander, et al., WO 98/26785, teaches use of an anti-glucocorticoid to treat schizophrenia and manic states. However, schizophrenia and manic states are are believed to be the result of abnormal nerve structure, i.e., "hard-wiring" problems. In contrast, it is believed that the pathophysiology of psychosis (the term used in its modern sense, as used in the instant invention) is related to neurochemical (glucocorticoid regulatory) problems. This theory is extended by the instant invention, in which it was surprisingly discovered that agents which inhibit the binding of cortisol to its receptor can be used to treat psychosis.

Today it is known that psychotic patients can be distinguished from other psychiatric problems in that they have a glucocorticoid regulatory dysfunction. In contrast, patients with schizophrenia and manic states do not have glucocorticoid regulatory dysfunction (see, e.g., Rothschild (1982) *Br. J. Psychiatry* 141:471–474; Clower (1986) *J. Clin. Psychopharmacol.* 6:363–365). Thus, schizophrenia and manic states are not within the scope of the definition of "psychosis" (as defined either by the medical profession, or, as used herein), and thus are not treated by the methods of the invention.

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which differs in only the last fifteen amino acids. The two types of GR have high affinity for their specific ligands, and are considered to function through the same transduction pathways.

The biologic effects of cortisol, including those caused by hypercortisolemia, can be modulated at the GR level using receptor antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a K of dissociation $\leq 10^{-9}$ M (Cadepond (1997) *Annu. Rev. Med.* 48:129).

Patients with some forms of psychiatric illnesses have been found to have increased levels of cortisol (Krishnan (1992) *Prog. Neuro-Psychophannacol. & Biol. Psychiat.* 16:913–920). For example, some patients with depressed mood have had their mood improve with treatments which lower the levels of cortisol. In some individuals, reversing increased cortisol levels using inhibitors of steroid biosynthesis can be effective in treating depression (Murphy (1991) *J. Steroid Biochem. Mol. Biol.* 39:239; Murphy (1991) *J. Clin. Psychopharmcol.* 11:121; Dhar (1989) *Clin. Invest. Med.* 12:B27). Alternatively, some depressed individuals can be responsive to treatments which block the effect of cortisol, as by administering GR antagonists (Van Look (1995) *Human Reproduction Update* 1:19–34). In one study, a patient with depression secondary to Cushing's Syndrome (hyperadrenocorticism) was responsive to a high dose, up to 1400 mg per day, of GR antagonist mifepristone (Nieman (1985) *J. Clin Endocrinol. Metab.* 61:536). Another study which used mifepristone to treat Cushing's syndrome found that it improved the patients' conditions, including their psychiatric status (Chrousos, pp 273–284, In: Baulieu, ed. The Antiprogestin Steroid RU 486 and Human Fertility Control. Plenum Press, New York (1989), Sartor (1996) *Clin. Obstetrics and Gynecol.* 39:506–510). Mifepristone has been used to treat major depression. Using from about 2.5 to 4.4 mg/kg per day for periods up to eight weeks, one group found that four patients with chronic severe depression, who were resistant to conventional therapies, responded to treatment (Murphy (1993) *J. Psychiatr. Neurosci.* 18:209).

Psychosis has also been associated with Cushing's syndrome (Gerson (1985) *Can. J. Psychiatry* 30:223–224; Saad (1984) *Am. J. Med.* 76:759–766). Mifepristone has been used to treat acute psychiatric disturbances secondary to Cushing's syndrome. One study showed that a relatively high dose of mifepristone (400 to 800 mg per day) was useful in rapidly reversing acute psychosis in patients with severe Cushing Syndrome due to adrenal cancers and ectopic secretion of ACTH from lung cancer (Van der Lely (1991) *Ann. Intern. Med.* 114:143; Van der Lely (1993) *Pharmacy World & Science* 15:89–90; Sartor (1996) supra).

Psychotic major depression has long been recognized as a distinct psychiatric illness, having both psychotic and depressive components. In a differential diagnosis, it is important that psychotic major depression be distinguished from nonpsychotic major depression, because effective treatments and patterns of response to pharmacologic therapies for psychotic major depression are very different from those relating to non-psychotic major depression. Successful treatment depends on the accuracy of the initial diagnosis. (Glassman (1981) *Arch. Gen. Psychiatry* 38:424–427, Schatzberg (1992) *Am. J. Psychiatry* 149:733–745, Schatzberg (1988) *Annals N.Y Acad. of Sci.*537:462). Psychotic major depression is very common. It has been estimated that twenty five percent of depressed patients admitted to the hospital have psychotic major depression (Coryell (1984) *J. Nerv. Ment.* Dis. 172:521).

Before this invention, there was to fast-acting effective treatment without significant side effects for the treatment of psychosis or the psychotic component of illnesses and conditions associated with psychosis, such as psychotic major depression. Individuals suffering from psychotic major depression have a low placebo response rate and respond poorly to antidepressant therapy alone, i.e., without concurrent treatment with antipsychotic medication (Glassman (1975) *Am. J. Psychiatry* 132:716–719; Avery (1979) *Am. J. Psychiatry* 135:559–562). While psychotic depression can respond to electroconvulsive therapy (ECT), this form of treatment is controversial, can have significant side effects, has a relatively slow response rate and has a high level of related morbidity. Similarly, another commonly used treatment for psychotic major depression, a combination therapy of currently available antipsychotic and antidepressant medications, has a slow onset of action and a relatively high rate of morbidity (Minter (1979) *J. Nerv. Ment. Dis.* 167:726–733).

Thus, there exists a great need for a more effective and safer treatment for psychosis and illnesses and conditions associated with psychosis, including psychotic major depression. There is a great need for a new treatment for psychotic major depression which has a quick response time, has few side effects, decreases the amount of time a patient must be institutionalized and has a lower rate of morbidity. Furthermore, there exists a variety of conditions which have a psychotic element for which there is no known cure or effective treatment. These include schizoaffective disorder, Alzheimer's Disease and cocaine addiction. Thus, there exists a great need for a safe and effective treatment for these conditions. The present invention fulfills these and other needs.

SUMMARY OF THE INVENTION

The invention is directed to a method of treating psychosis associated with glucocorticoid related dysfunction by administration of an amount of a glucocorticoid receptor antagonist effective to ameliorate the psychosis, with the proviso that the patient not be suffering from Cushing's Syndrome. In alternative embodiments of this method, the psychosis is associated with psychotic major depression, schizoaffective disorder, Alzheimer's Disease and cocaine addiction.

In further embodiments, the glucocorticoid receptor antagonist used in the methods can comprise a steroidal skeleton with at least one phenyl-containing moiety in the 11-beta position of the steroidal skeleton. The phenyl-containing moiety in the 11-beta position of the steroidal skeleton can be a dimethylaminophenyl moiety.

In alternative embodiments of the invention, the glucocorticoid receptor antagonist can comprise mifepristone (RU486), RU009 or RU044. The glucocorticoid receptor antagonist can be administered in a daily amount of between about 8 to 20 mg per kilogram of body weight per day, or, in a daily amount of about 8 to 12 mg per kilogram of body weight per day. The glucocorticoid receptor antagonist can be administered for about four days. It can be administered in a daily amount of about 600 mg per day. The administration can be once per day. Its mode of administration can be oral or transdermal.

In a preferred embodiment, the invention relates to a method of ameliorating psychotic depression comprising administering a mifepristone in a daily amount of about 8 to 12 mg per kilogram of body weight per day, wherein the administration continues for a period of about four days.

The invention also relates to a kit for the amelioration of psychosis in a human, the kit comprising: a glucocorticoid receptor antagonist; and, an instructional material teaching the indications, dosage and schedule of administration of the glucocorticoid receptor antagonist. The kit's instructional material can indicate that the glucocorticoid receptor antagonist can be administered in a daily amount of about 8 to 12 mg per kilogram of body weight per day. The instructional material can indicate that the administration of the glucocorticoid receptor antagonist can continue for a period of about four days.

In one embodiment, the kit is for the amelioration of psychosis as a component of psychotic major depression and the instructional material indicates that the glucocorticoid receptor antagonist can be used for the treatment of psychotic major depression. In a preferred embodiment, the kit's glucocorticoid receptor antagonist is mifepristone, which can be in tablet form.

The invention also relates to a novel means of diagnosing and assessing treatments for psychosis using color-word recognition tests. In one embodiment, the Stroop Color and Word Test, or variations thereof, is used to objectively determine whether an individual is psychotic, the degree of psychosis and the efficacy of an antipsychotic treatment regimen. The invention also provides a color-word test to differentially diagnose psychotic major depression from non-psychotic major depression.

A further understanding of the nature and advantages of the present invention is realized by reference to the remaining portions of the specification, the figures and claims.

All publications, patents and patent applications cited herein are hereby expressly incorporated by reference for all purposes.

DEFINITIONS

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation. For example, a clinical guide to monitor the effective amelioration of a psychiatric disorder, such as psychosis or depression, is found in the Structured Clinical Interview for DSM-IV Axis I mood disorders ("SCID-P") (see fourth edition of *Diagnostic and Statistical Manual of Mental Disorders* (1994) Task Force on DSM-IV, American Psychiatric Association ("DSM-IV"); Kaplan, Ed. (1995) *Comprehensive Textbook of Psychiatry/VI*, vol. 1, sixth ed., pp 621–627, Williams & Wilkins, Balt., Md.).

The term "glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "glucocorticoid receptor antagonist" also refers to any composition or compound which inhibits any biological response associated with the binding of a GR to an agonist.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "cortisol" refers to a family of compositions also referred to hydrocortisone, and any synthetic or natural analogues thereof.

The term "mifepristone" refers to a family of compositions also referred to as RU486, or RU38.486, or 17-beta-hydroxy-11-beta-(4-dimethyl-aminophenyl)-17-alpha (1-propynyl)-estra-4,9-dien-3-one), or 11-beta-(4dimethylaminophenyl)-17-beta-hydroxy17-alpha-(1-propynyl)-estra-4,9-dien-3-one), or analogs thereof, which bind to the glucocorticoid receptor, typically with high affinity, and inhibit the biological effects initiated/mediated by the binding of any cortisol or cortisol analogue to a receptor.

Chemical names for RU-486 vary; for example, RU486 has also been termed:

11B-[p-(Dimethylamino)phenyl]-17B-hydroxy-17-(1-propynyl)-estra-4,9-dien-3-one;

11B-(4-dimethyl-aminophenyl)-17B-hydroxy-17A-(prop-1-ynyl)-estra-4,9-dien-3-one;

17B-hydroxy-11B-(4-dimethylaminophenyl-1)-17A-(propynyl-1)-estra-4,9-diene-3-one;

17B-hydroxy-11B-(4-dimethylaminophenyl-1)-17A-(propynyl-1)-E; (11B,17B)-11-[4-dimethylamino)-phenyl]-17-hydroxy-17-(1-propynyl)estra-4,9-dien-3-one; and 11B-[4-(N,N-dimethylamino)phenyl]-17A-(prop-1-ynyl)-D-4,9-estradiene-17B-ol-3-one.

The term "psychotic" as used herein refers to a psychiatric condition in its broadest sense, as defined in the DSM-IV (Kaplan, ed. (1995) supra) and described below. The term "psychotic" has historically received a number of different definitions, ranging from narrow to broadly described. A psychotic condition can include delusions or prominent hallucinations, including prominent hallucinations that the individual realizes are hallucinatory experiences, and those with hallucinations occurring in the absence of insight into their pathological nature. Finally, the term includes a psychotic condition characterized by a loss of ego boundaries or a gross impairment in reality testing. Unlike this definition, which is broad and based primarily on symptoms, characterization of psychosis in earlier classifications (e.g., DSM-II and ICD-9) were more inclusive and focused on the severity of functional impairment (so that a mental disorder was termed "psychotic" if it resulted in "impairment" that grossly interferes with the capacity to meet ordinary demands of life). Different disorders which have a psychotic component comprise different aspects of this definition of "psychotic." For example, in schizophreniform disorder, schizoaffective disorder and brief psychotic disorder, the term "psychotic" refers to delusions, any prominent hallucinations, disorganized speech, or disorganized or catatonic behavior. In psychotic disorder due to a general medical condition and in substance-induced psychotic disorder, "psychotic" refers to delusions or only those hallucinations that are not accompanied by insight. Finally, in delusional disorder and shared psychotic disorder, "psychotic" is equivalent to "delusional" (see DSM-IV, supra, page 273).

Objective tests can be also be used to determine whether an individual is psychotic and to measure and assess the success of a particular treatment schedule or regimen. For example, measuring changes in cognitive ability aids in the diagnosis and treatment assessment of the psychotic patient. Any test known in the art can be used, such as the so-called "Wallach Test," which assesses recognition memory (see below, Wallach (1980) *J. Gerontol.* 35:371–375). For example, as described in Example 1, when the Wallach Recognition Test was used to measure the degree of amelioration of psychosis in the study's subjects, on the average, test subjects identified fewer distracters over words they had actually heard before. The number of distracting words misidentified as words actually presented in the test declined between 25% and 100% after treatment. Another example of an objective text which can be used to determine whether an individual is psychotic and to measure efficacy of an antipsychotic treatment is the Stroop Color and Word Test ("Stroop Test") (see Golden, C. J., Cat. No. 30150M, In *A Manual for Clinical and Experimental Uses*, Stoelting, Wood Dale, Ill.). The Stroop Test is an objective neuropsychiatric test that can differentiate between individuals with psychosis and those without, and is described in detail below.

The term "psychosis" refers to a psychiatric symptom, condition or syndrome in its broadest sense, as defined in the DSM-IV (Kaplan, ed. (1995) supra), comprising a "psychotic" component, as broadly defined above. The term psychosis can refer to a symptom associated with a general medical condition, a disease state or other condition, such as a side effect of drug abuse (a substance-induced disorder) or as a side effect of a medication. Alternatively, the term psychosis can refer to a condition or syndrome not associated with any disease state, medical condition, drug intake or the like.

Psychosis is typically defined as a mental disorder or condition causing gross distortion or disorganization of a person's mental capacity, affective response, and capacity to recognize reality, communicate, and relate to others to the degree of interfering with his capacity to cope with the ordinary demands of everyday life.

Historically, the term "psychosis" was sometimes used to describe schizophrenia and manic states (these conditions are separately described in the DSM-IV, supra). However, the current medical view, as embraced by the DSM-IV, supra, does not include these psychiatric conditions as including psychosis. There is a physiologic basis for this discrimination, which was recognized as early as Rothschild, et al. (1982) "The dexamethasone suppression test as a discriminator among subtypes of psychotic patients," *Br. J. Psychiatry* 141:471–474; and, Clower (1986) "The 2-mg dexamethasone suppression test in differentiating major depression with psychosis from schizophrenia," *J. Clin. Psychopharmacol.* 6:363–365. The dexamethasone suppression (DS) test indicates a dysfunction in the glucocorticoid regulatory feedback pathway, which is controlled by the hypothalamic-pituitary-adrenal (HPA) axis (non-responsiveness in the test means a patient cannot suppress (negatively feedback) cortisol production when challenged with a test dose of a synthetic glucocorticoid, dexamethasone). Most psychotic patients have a glucocorticoid regulatory dysfunction (as indicated by non-responsiveness in the DS test). In contrast, patients with, e.g., schizophrenia (including those historically described as "psychotic schizophrenics") and manic states, do not have glucocorticoid regulatory dysfunction (as indicated by responsiveness in the DS test). It is widely believed that schizophrenia and manic states are caused by abnormal nerve structure, i.e., a "hardwiring" problem. In contrast, it is believed that the pathophysiology of psychosis is related to neurochemical problems, particularly, HPA axis regulatory dysfunction (this theory is extended by the instant invention, in which it was discovered that that agents which inhibit the binding of cortisol to its receptor will treat psychosis). Thus, schizophrenia and manic states are not within the scope of the definition of "psychosis" (as defined either by the medical profession, or, as used herein), and thus are not treated by the methods of the invention.

The term "psychotic major depression," also referred to as "psychotic depression" (Schatzberg (1992) *Am. J. Psychiatry* 149:733–745), "psychotic (delusional) depression" (Ibid.), "delusional depression" (Glassman (1981) supra) and, "major depression with psychotic features" (see the DSM-III-R), refers to a distinct psychiatric disorder which includes both depressive and psychotic features. Individuals manifesting both depression and psychosis, i.e. psychotic depression, are herein referred to as "psychotic depressives." It has been long-recognized in the art as a distinct syndrome, as described, for example, by Schatzberg (1992) supra. Illustrative of this distinctness are studies which have found significant differences between patients with psychotic and nonpsychotic depression in glucocorticoid activity, dopamine-beta-hydroxylase activity, levels of dopamine and serotonin metabolites, sleep measures and ventricle to brain ratios. Psychotic depressives respond very differently to treatment compared to individuals with other forms of depression, such as "non-psychotic major depression." Psychotic depressives have a low placebo response rate and a respond poorly to antidepressant therapy alone (without concurrent anti-psychotic treatment). Psychotic depressives are markedly unresponsive to tricyclic (anti-depressive) drug therapy (Glassman, et al. (1975) supra). While psychotic depressives can respond to electroconvulsive therapy (ECT), their response time is relatively slow and the ECT has a high level of related morbidity. Clinical manifestations and diagnostic parameters of "psychotic major depression" is described in detail in the DSM-IV (Kaplan, ed. (1995) supra). Thus, due to its unique pathophysiology, high rate of morbidity and response to treatment, there is great practical need to differentially diagnose and specifically treat psychotic major depression as compared to non-psychotic depression.

DETAILED DESCRIPTION OF THE INVENTION

This invention pertains to the discovery that agents that can inhibit a biological response caused by an agonist-occupied glucocorticoid receptor (GR) are effective for ameliorating the mental disorder, or syndrome, of psychosis. Because the condition of psychosis can be associated with or caused by a variety of conditions and disease processes, the methods of the invention also are used to ameliorate the psychotic component of pathologies or conditions involving psychosis. These pathologies or conditions include psychotic major depression, schizoaffective disorders, Alzheimer's Disease, cocaine addiction, drug side effects and the like.

In one embodiment, the methods of the invention use agents that act as GR antagonists, blocking the interaction of cortisol with GR, thereby ameliorating psychosis. In another embodiment, mifepristone, a potent GR antagonist, is used in methods to ameliorate psychosis. The invention provides a new, effective treatment for psychotic major depression which is relatively fast, has fewer side effects, decreases the amount of time a patient must be institutionalized and has a lower rate of morbidity when compared to alternative treatments.

As psychosis can be manifested as a mental illness in the form of a syndrome or as an element of a disease process or other condition, various means of diagnosing and assessing the success of treatment, i.e., the success and extent the psychosis is ameliorated, are set forth below. These means include classical psychological evaluations and various laboratory procedures. As the methods of the invention include use of any means to inhibit the biological effect of a GR to ameliorate psychosis, illustrative compounds and compositions which can be used to treat psychosis are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

1. GENERAL LABORATORY PROCEDURES

A number of general laboratory tests can be used to assist in the diagnosis, progress and prognosis of the patient. Monitoring of parameters such as blood cortisol, drug metabolism, brain function and the like may be needed because all patients metabolize and react to drugs uniquely. In addition, such monitoring may be important because each GR antagonist has different pharmacokinetics. Different disease conditions may require different dosage regimens and formulations. Such procedures are well described in the scientific and patent literature. A few illustrative examples are set forth below.

a. Determining Blood Cortisol Levels

Because levels of blood cortisol have been associated with psychosis and depression, monitoring blood cortisol levels can be a useful laboratory test to aid in the diagnosis, treatment and prognosis of the patient. A wide variety of laboratory tests exist that can be used to determine whether an individual is normal, hypo- or hypercortisolemic. Immunoassays such as radioimmunoassays are commonly used because they are accurate, easy to do and relatively cheap. Because levels of circulating cortisol is an indicator of adrenocorticol function, a variety of stimulation and suppression tests, such as ACTH Stimulation, ACTH Reserve, Dexamethasone Suppression, can also provide diagnostic, prognostic or other information to be used adjunctively in the methods of the invention.

One such assay available in kit form is the radioimmunoassay available as "Double Antibody Cortisol Kit™" (Diagnostic Products Corporation, Los Angeles, Calif., (1984) *Acta Psychiatr. Scand.* 70:239–247). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 1, below.

i. Determining Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to ameliorate psychosis, an illustrative example of determining blood and urine mifepristone levels is set forth below.

ii. Other Laboratory Procedures

Because psychosis can be associated with a variety of diseases, conditions, and drug effects, a number of additional laboratory tests can be used adjunctively in the methods of the invention to assist in diagnosis, treatment efficacy, prognosis, toxicity and the like. For example, as increased hypercortisolemia has been associated with psychosis and depression, diagnosis and treatment assessment can be augmented by monitoring and measuring glucocorticoid-sensitive variables, including but limited to fasting blood sugar, blood sugar after oral glucose administration, plasma concentrations thyroid stimulating hormone (TSH), corticosteroid-binding globulin, luteinizing hormone (LH), testosteroneestradiol-binding globulin, and/or total and free testosterone. Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai (1987) *Pharmacol. and Experimental Therapeutics* 241:401–406.

2. GLUCOCORTICOID RECEPTOR ANTAGONISTS TO TREAT PSYCHOSIS

The invention provides for methods of treating psychosis utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

a. Steroidal Anti-Glucocorticoids as GR Antagonists.

In one embodiment of the invention, steroidal glucocorticoid antagonists are administered for the amelioration of psychosis. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain. (Lefebvre (1989) *J. Steroid Biochem.* 33:557–563).

i. Removal or Substitution of the 11-beta Hydroxy Group

In another embodiment of the invention, glucocorticoid agonists with modified steroidal backbones comprising removal or substitution of the 11-beta hydroxy group are administered. This class includes natural antiglucocorticoids, including cortexolone, progestertone and testosterone derivatives, and synthetic compositions, such as mifepristone (Lefebvre, et al. (1989) Ibid). Preferred embodiments of the invention include all 11-beta-aryl steroid backbone derivatives because these compounds are devoid of progesterone receptor (PR) binding activity (Agarwal (1987) *FEBS* 217:221–226). Another preferred embodiment comprises an 11-beta phenyl-aminodimethyl steroid backbone derivative, i.e., mifepristone, which is both an effective anti-glucocorticoid and anti-progesterone agent.

These compositions act as reversibly-binding steroid receptor antagonists For example, when bound to a 11-beta phenyl-aminodimethyl steroid, the steroid receptor is maintained in a conformation that cannot bind its natural ligand, such as cortisol in the case of GR (Cadepond, et al., (1997), supra).

Synthetic 11-beta phenyl-aminodimethyl steroids include mifepristone, also known as RU486, or 17-beta-hydrox-11-beta-(4-dimethyl-aminophenyl) 17-alpha-(1-propynyl)estra-4,9-dien-3-one). It has been shown to be a powerful antagonist of both the progesterone and glucocorticoid (GR) receptors: Another 11-beta phenyl-aminodimethyl steroids shown to have GR antagonist effects includes RU009 (RU39.009), 11-beta-(4-dimethyl-aminoethoxyphenyl)-17-alpha-(propynyl-17 beta-hydroxy-4,9-estradien-3-one) (see Bocquel (1993) *J. Steroid Biochem. Molec. Biol.* 45:205–215). Another GR antagonist related to RU486 is RU044 (RU43.044) 17-beta-hydrox-17-alpha-19-(4-methylphenyl)-androsta-4,9 (11)-dien-3-one) (Bocquel (1993) supra). See also Teutsch (1981) *Steroids* 38:651–665; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta, 17- alpha, 21-triol-3, 20-dione-21-methane-sulfonate and dexamethasone-21-mesylate (16-methyl-9 alpha-fluoro-1,4-pregnadiene-11 beta, 17-alpha, 21-triol-3, 20-dione-21-methane-sulfonate). See Simons (1986) *J. Steroid Biochem.* 24:25–32 (1986); Mercier (1986) *J. Steroid Biochem.* 25:11–20; U.S. Pat. No. 4,296,206.

ii. Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre (1989) supra; Rousseau (1979) *Nature* 279:158–160).

iii. Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne (1980) *Endocrinology* 107:1278–1280).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoidal activity in comparison to 17-propinyl side chain containing compounds.

b. Non-Steroidal Anti-Glucocorticoids as Antagonists.

Non-steroidal glucocorticoid antagonists are also used in the methods of the invention to ameliorate psychosis. These include synthetic mimetics and analogs of proteins, including partially peptidic, pseudopeptidic and non-peptidic molecular entities: For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (de Bont (1996) *Bioorganic & Medicinal Chem.* 4:667–672). The creation and simultaneous screening of large libraries of synthetic molecules can be carried out using well-known techniques in combinatorial chemistry, for example, see van Breemen (1997) *Anal Chem* 69:2159–2164; Lam (1997) *Anticancer Drug Des* 12:145–167 (1997). Design of peptidomimetics specific for GR can be designed using computer programs in conjunction with combinatorial chemistry (combinatorial library) screening approaches (Murray (1995) *J. of Computer-Aided Molec. Design* 9:381–395); Bohm (1996) *J. of Computer-Aided Molec. Design* 10:265–272). Such "rational drug design" can help develop peptide isomerics and conformers including cycloisomers, retro-inverso isomers, retro isomers and the like (as discussed in Chorev (1995) *Tib Tech* 13:438–445).

c. Identifying Glucocorticoid Receptor Antagonists

Because any GR antagonist can be used for the amelioration of psychosis in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner (1970) *Meth. Enzymol.* 15:633. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in raw extracts. TAT converts the amino group of tyrosine to 2-oxoglutaric acid, and p-hydroxyphenylpyruvate is also formed, which is converted to the more stable p-hydroxybenzaldehyde in alkaline solution, which can be measured at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany (1986) "Glucocorticoid regulation of hepatic cytosolic glucocorticoid receptors in vivo and its relationship to induction of tyrosine aminotransferase," *Biochem. Biophys. Acta* 886:162–168).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, for example, Choi (1992) "Enzyme induction and receptor-binding affinity of steroidal 20-carboxamides in rat hepatoma tissue culture cells," *Steroids* 57:313–318). As another example, the ability of a putative GR antagonist to block nuclear binding of $^3$H-dexamethasone-GR complex can be used (Alexandrova (1992) "Duration of antagonizing effect of RU486 on the agonist induction of tyrosine arminotransferase via glucocorticoid receptor," *J. Steroid Biochem. Mol. Biol.* 41:723–725). To further identify putative GR antagonists, kinetic assays able to discriminate between glucocorticoid agonists and antagonists by means of receptor-binding kinetics can also be used (as described in Jones (1982) *Biochem J.* 204:721–729).

In another illustrative example, the assay described by Daune (1977) *Molec. Pharm.* 13:948–955, and in U.S. Pat. No. 4,386,085, can be used to identify antiglucocorticoid activity. Briefly, the thymocytes of surrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. Nos. 4,296,206 (see above); 4,386,085 (see above); 4,447,424; 4,477,445; 4,519, 946; 4,540,686; 4,547,493; 4,634,695; 4,634,696; 4,753, 932; 4,774,236; 4,808,710; 4,814,327; 4,829,060; 4,861, 763; 4,912,097; 4,921,638; 4,943,566; 4,954,490; 4,978, 657; 5,006,518; 5,043,332; 5,064,822; 5,073,548; 5,089, 488; 5,089,635; 5,093,507; 5,095,010; 5,095,129; 5,132, 299; 5,166,146; 5,166,199; 5,173,405; 5,276,023; 5,380, 839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1, 2-dihydro N-1 protected quinolines.

3. DIAGNOSING AND ASSESSING CONDITIONS AND ILLNESSES INVOLVING PSYCHOSIS

Psychosis can be manifested as a mental illness in the form of a syndrome or as an element of a variety of disease processes. There are various means to diagnose these various forms of psychosis and assess the success of treatment. These means include classical psychological evaluations in addition to the various laboratory procedures described above. Such means are well-described in the scientific and patent literature, and some illustrative examples are provided below.

a. Assessing and diagnosing psychosis

The psychosis ameliorated in the methods of the invention encompasses a broad range of mental conditions and symptoms, as broadly described in the DSM-IV (Kaplan, ed. (1995) supra). Psychosis can refer to a symptom associated with a general medical condition, a disease state or other condition, such as a side effect of drug abuse (a substance-induced disorder) or as a side effect of a medication. While the practitioner can use any set of proscribed or empirical criteria to diagnose the presence of a psychosis as an indication to practice the methods of the invention, some illustrative diagnostic guidelines and examples of relevant symptoms and conditions are described below.

Psychosis can be diagnosed by formal psychiatric assessment using, for example, a semi-structured clinical interview described as "The Structured Clinical Interview for DSM-II-R, or "SCID." SCID is designed to be administered by clinicians and researchers familiar with the diagnostic criteria used in the DSM-II-R (the revised third edition of DSM). The SCID has two parts, one for Axis I disorders (clinical disorders and other conditions that may be a focus of clinical attention) and another for Axis II personality disorders (personality disorders and mental retardation) (see DSM-IV, supra, pgs 25–31, for a general description of a "multiaxial assessment system" to guide clinicians in planning treatment and predicting outcome). At the start of the SCID interview, an overview of the present illness, chief complaint, and past episodes of major psychopathology are obtained before systematically asking the patient questions about specific symptoms. The interview schedule itself has many questions which are openended so that patients have an opportunity to describe symptoms in their own words.

At the conclusion of the interview, the interviewer also completes the Global Assessment of Functioning (GAF) scale, the fifth ("V") Axis on DSM-IV's multiaxial assessment system. Axis V is for reporting the clinician's judgment of the individual's overall level of functioning. This information is useful in planning treatment and measuring its impact, and in predicting outcome. The GAF scale is particularly useful in tracking the clinical progress of individuals in global terms using a single measure (see DSM-IV, supra, pages 30 to 31; Kaplan, ed. (1995), supra). In some settings, it may be useful to assess social and occupational disability and to track progress in rehabilitation independent of the severity of the psychological symptoms. For this purpose, use, for example, the proposed Social and Occupational Functioning Assessment Scale (SOFAS) DSM-IV, supra, pg. 760, Appendix B. Additional assessment schemes can be used, for example, the Global Assessment of Relational Functioning (GARF) Scale (DSM-IV, supra, pg 758, Appendix B) or the Defensive Functioning Scale (DSM-IV, supra, pg 751, Appendix B).

To assess the progress of a treatment for psychosis or aid in its diagnosis or prognosis, the "Brief Psychiatric Rating Scale (BPRS)" can also be used after the semistructured interview with the patient. The BPRS is an 18-dimension rating scale. Each dimension represents a domain of behavior and psychiatric symptoms, such as anxiety, hostility, affect, guilt and orientation. These are rated on a seven-point "Likert Scale" from "not present" to "extremely severe." The BPRS is brief, easily learned and provides a quantitative score that reflects global pathology. The BPRS is useful in providing a crude barometer of a patient's overall benefit from treatment, and thus is useful in assessing changes in an individual's condition after treatment and amelioration using the methods of the invention (Overall (1962) *Psychol. Rep.* 10:799; Kaplan (1995), supra).

Objective tests can be also be used with these subjective, diagnostic criteria to determine whether an individual is psychotic and to measure and assess the success of a particular treatment schedule or regimen. Diagnosis, categorization, or assessment of treatment of psychosis or any psychiatric condition can be objectively assessed using any test known in the art, such as that described by Wallach (1980) *J. Gerontol.* 35:371–375, or the Stroop Color and Word Test.

The so-called "Wallach Test" can measure the presence and degree of psychosis by evaluating cognitive changes in the individual. The test assesses recognition memory, as described above. As discussed in Example 1, the Wallach Recognition Test was used to measure the degree of amelioration of psychosis in the study's subjects.

The Stroop Color and Word Test ("Stroop Test") is another means to objectively determine whether an individual is psychotic and to measure efficacy of treatment (see Golden, supra). The Stroop Test can differentiate between individuals with psychosis and those without. Briefly, the test developed from the observation that the naming of colors is always slower than the reading of color names in literate adults. For instance, it always takes less time to read the printed word "yellow" than it does to recognize what color a word is printed in (for example, "XXX" printed in yellow ink). Furthermore, if color words are printed in non-matching colored inks (as, the word yellow in red ink), it takes a normal individual 50% longer to name the proper color (red) than if they are shown only the color (such as a red rectangle, or "XXX" in red). This delay in color recognition is called "the color-word interference effect" and is the time is the variable parameter measured in the Stroop Test. The greater the delay, the lower the Stroop Test score (see also Uttl (1997) *J. Clin. Exp. Neuropsychol.* 19:405–420). Individuals with psychosis have statistically significantly lower scores on the Stroop Test than individuals without psychosis. Importantly, patients with psychotic major depression have statistically significantly lower scores than those with major depression, further confirming the finding that psychotic major depression is a distinct condition as compared to non-psychotic severe depression.

Psychiatric conditions, such as psychosis, can be further diagnosed and evaluated using any of the many tests or criteria well-known and accepted in the fields of psychology or psychiatry.

The features (symptoms) of and criteria for diagnosing psychotic disorders, such as psychotic major depression, are further described DSM-IV, supra. While the practitioner can use any criteria or means to evaluate whether an individual is psychotic to practice the methods of the invention, the DSM-IV sets forth a generally accepted standard for such diagnosing, categorizing and treating of psychiatric disorders, including psychosis. Several illustrative examples of such criteria utilized in the methods of the invention are set forth below.

Psychosis is typically characterized as a mental disorder or condition causing gross distortion or disorganization of a person's mental capacity, affective response, and capacity to recognize reality, communicate, and relate to others to the degree of interfering with his capacity to cope with the ordinary demands of everyday life. In a condition or illness involving psychosis, delusions or hallucinations can be present. The content of the delusions or hallucinations have many depressive themes. In psychotic major depression there can be "mood-congruent" psychotic features, including, for example, delusions of guilt, delusions one deserves punishment (e.g. because of a personal inadequacy or moral transgression), nihilistic delusions (e.g. of world or personal destruction), somatic delusions (e.g. having cancer), or delusions of poverty. Hallucinations, when present in psychotic major depression are usually transient and not elaborate and may involve voices that berate the patient for shortcomings or sins. More rarely, the content of the delusions or hallucinations has no apparent relationship to depressive themes. In this situation these "mood-incongruent" psychotic features include, for example, grandiose delusions.

Psychosis can include bipolar I disorder with psychotic features. The essential feature of this disorder is a clinical course that is characterized by the occurrence of one or more manic episodes or mixed episodes. Often individuals have also had one or more major depressive episodes. In addition, the episodes are not better accounted for by schizoaffective disorder and are not superimposed on schizophrenia, schizophreniform disorder, delusional disorder or psychotic disorder not otherwise specified (see DSM-IV, supra, pages 350–352, 320, 328, 333). In bipolar I disorder with psychotic features, delusions or hallucinations, typically auditory, are also present. The content of the delusions or hallucinations commonly have a manic theme. The features can be "mood-congruent" psychotic features, including for example delusions that God's voice can be heard explaining the person has a special mission or persecutory delusions. More rarely, the content of the delusions or hallucinations has no apparent relationship to manic themes. In this situation these "mood-incongruent" psychotic features include the same as those described for "mood-congruent" features of severe depression with psychotic features.

A condition or illness involving psychosis can also include brief psychotic disorder, in which one or more of the following symptoms can be present: delulsions, hallucinations, disorganized speech (e.g. frequent derailment or incoherence) and grossly disorganized or catatonic behavior. Duration of an episode of the disturbance is at least one day but less than one month.

Psychosis can also be classified as "delusional disorder." According to DSM IV, diagnostic criteria for delusional disorder includes: nonbizarre delusions of at least one month's duration; criteria A for schizophrenia has never been met, apart from the impact of the delusions; functioning is not markedly impaired; and, behavior is not obviously odd or bizarre.

A condition or illness involving psychosis can be classified as "shared psychotic disorder." According to DSM IV, the diagnostic criteria for shared psychotic disorder includes: a delusion in the context of a close relationship with another person who has an already-established delusion; the delusion is similar in content to that of the person who already has the established delusion; and, the disturbance is not better accounted for by another psychotic disorder (e.g. schizophrenia) or a mood disorder with psychotic features, and, is not due to the direct physiological effects of a substance or general medical condition.

A condition or illness involving psychosis can be classified as a "substanceinduced" psychotic disorder. According to DSM IV criteria, there must be evidence of recent or prolonged substance use, withdrawal from a substance or exposure to a toxin. Alternatively, a condition or illness involving psychosis can also be classified as a "psychotic disorder due to a general medical condition." According to DSM IV criteria, there must be: evidence from the history, physical examination or laboratory findings that the disturbance is the direct physiological consequence of a general medical condition, prominent hallucinations or delusions, the disturbance is not better accounted for by another mental disorder, and, the disturbance does not occur exclusively during the course of a delirium.

A condition or illness involving psychosis can be classified as a psychotic disorder not otherwise specified. According to DSM IV criteria, this category includes psychotic symptomology (i.e. delusions, hallucinations, disorganized speech, grossly disorganized or catatonic behavior) about which there is inadequate information to make a specific diagnosis or about which there is contradictory information, or disorders with psychotic symptoms that do not meet the criteria for any specific psychotic disorder. Examples include: postpartum psychosis that does not meet other DSM IV categories; psychotic symptoms that have lasted for less than one month but have not yet remitted; persistent auditory hallucinations in the absence of other features; persistent nonbizarre delusions with period of overlapping mood episodes that have been present for a substantial portion of the delusional disturbance; and, situations in which the clinician has concluded that a psychotic disorder is present but is unable to determine whether it is primary, due to general medical condition or is substance-induced.

b. Assessing and diagnosing depression

The psychotic component of psychotic major depression, which has elements of psychosis and depression, is ameliorated by the methods of the invention. Other conditions and illnesses with some degrees or forms of depression associated with psychosis are also ameliorated by the methods of the invention. Thus, in practicing some embodiments of the invention the practitioner should be aware of means to assess and diagnose depression. Such criteria are well known in the art, and some illustrative examples are set forth below.

Diagnosis of depression can be assisted by formal psychiatric assessment using a structured interview instrument like the SCID (discussed above), as well as a measure of the degree of depressive symptoms, such as, for example, the Hamilton Rating Scale for Depression ("HAM-D") (Hamilton (1962) *J. Aeurol. Psychiatry* 23:56–62, Avery (1979) *Am. J. Psychiatry* 135:559–562), a widely used scale. The HAM-D is scored on the basis of a semistructured interview. The patient is rated on depression-related symptoms, including psychomotor retardation, insomnia, mood and insight. Several forms of depression with different numbers of symptoms ratings exist, leading to some confusion. However, the combined score correlates highly with the degree of depression severity. The rating scale is effective in monitoring a depressed state over time and is useful as an index of treatment effectiveness. The Hamilton Rating Scale can be used with an additional assessment device that focuses on the mood, affective, and cognitive changes known to accompany major depression (Kaplan, et al., (1995), supra).

As with psychosis, the "Brief Psychiatric Rating Scale (BPRS)" can also be used to diagnose or evaluate the efficacy of a treatment for depression in conjunction with the semi-structured interview. The BPRS is useful in providing a crude barometer of a patient's overall benefit from treatment, and thus is useful in assessing changes in an individual's condition after treatment and amelioration using the methods of the invention (Overall (1962) supra; Kaplan (1995), supra). Also as with psychosis, depression can be assessed by evaluating cognitive changes using any test known in the art, such as that described by Wallach (1980) *J. Gerontol.* 35:371–375. The so-called "Wallach Test" assesses recognition memory. Psychiatric conditions, such as depression, can be further diagnosed and evaluated using any of the many tests or criteria well-known and accepted in the fields of psychology or psychiatry.

c. Assessing and Diagnosing Schizoaffective Disorder

The psychotic component of schizoaffective disorder is ameliorated by the methods of the invention. The diagnostic criteria for schizoaffective disorder includes: an uninterrupted period of illness during which, at some time, there is either a major depressive episode, a manic episode or a mixed episode concurrent with symptoms that meet the criteria for schizophrenia. In schizoaffective disorder there must be: a mood episode that is concurrent with the active-phase symptoms of schizophrenia; mood symptoms must be present for a substantial portion of the total duration of the disturbance; and, delusions or hallucinations must be present for at least two weeks in the absence of prominent mood symptoms. In contrast, mood symptoms in schizophrenia either have a duration that is brief relative to the total duration of the disturbance, occur only during the prodromal or residual phases, or do not meet full criteria for a mood episode. The diagnostic criteria for schizophrenia include characteristic symptoms, social or occupational dysfunction, and/or persistence of symptoms. The "schizophrenia" criteria for schizoaffective disorder can also be classified as "schizophreniform disorder," which is diagnosed if the DSM IV criteria A, D and E of schizophrenia are met. An episode of this disorder lasts at least one month but less than six months. See also: Sharma (1997) *Am. J. Psychiatry* 154:1019–1021; McElroy (1991) *J. Clin. Psychiatry* 52:411–414.

The "Brief Psychiatric Rating Scale (BPRS)" can also be used after the semi-structured interview with the patient to evaluate schizophrenia and distinguish it from schizophreniform disorder (SD) and the psychosis associated with SD, as treated by the methods of the invention (Overall (1962) supra; Kaplan (1995), supra). It can be used to access changes in condition after treatment and amelioration when utilizing the methods of the invention (Kaplan (1995), supra).

d. Diagnosing and Assessing Alzheimer's Disease Related Psychosis

Psychosis associated with senile dementias and Alzheimer's disease is ameliorated by the methods of the invention. Behavioral changes are common in Alzheimer's disease and include psychosis, agitation, depression, anxiety, personality alterations, and neurovegetative changes. See Engelborghs (1997) *Acta Neurol. Belg.* 97:67–84; Cummings (1996) Neurology 47:876–883; Samson (1996) *Eur. Neurol.* 36:103–106.

Criteria to assess and diagnose psychosis associated with Alzheimer's Disease are the same as those used for psychosis, as described in Section 3.a, above.

e. Diagnosing and Assessing Drug-Related Psychosis

Psychosis associated with substance abuse or psychosis as a side-effect of medication is ameliorated by the methods of the invention. For example, psychosis is associated with cocaine abuse and addiction. Thus, the GR antagonists of the invention, such as mifepristone, can be used as a treatment for cocaine-induced psychosis. In another embodiment, the methods of the invention can treat cannabis-induced chronic psychosis, see Longhurst (1997) *Aust. N. Z. J. Psychiatry* 31:304–305. See also Evans (1997) "Drug induced psychosis with doxazosin," *BMJ3* 14:1869; Bhatia (1996) "Chloroquine—induced recurrent psychosis," Indian *J. Med. Sci.* 50:302–304; Scurlock (1996) "Another case of nicotine psychosis" *Addiction* 91:1388; Cohen (1996) "Substance-induced psychosis" *Br. J. Psychiatry* 168:651–652; Popli (1997) "Sertraline and psychotic symptoms: a case series," *Ann. Clin. Psychiatry* 9:15–17; Schreiber (1997) "Metronidazole-induced psychotic disorder," *Am. J. Psychiatry* 154:1170–1171.

Criteria to assess and diagnose psychosis associated with drug abuse and drug addiction are the same as those used for psychosis, as described in Section 3as above.

f. Other Psychosis-Associated Conditions

The anti-psychotic GR antagonists and methods of the invention can be effective in treating psychotic aggressive patients, conduct-disordered children, and mentally retarded patients. See Fava (1997) *Psychiatr. Clin. North Am.* 20:427–451. In another embodiment, the methods of the invention can be used as a adjunct in treating AIDS patients with psychiatric disorders, as psychosis secondary to AIDS infection is common (see Susser (1997) *Am. J. Psychiatry* 154:864–866; Schiff(1997) *N. Engl. J. Med.* 336:1190). In another embodiment, the methods of the invention can be used to treat psychosis associated with Parkinson's disease. Many patients with Parkinson's disease and dementia experience psychosis and psychotic symptoms. In Parkinson's disease, dementia is associated with major behavioral, cognitive, and functional problems (Nainark (1996) "Psychotic symptoms in Parkinson's disease patients with dementia." *J. Am. Geriatr. Soc.* 44:296–299. Means to diagnose these conditions are well known in the art and are described in these references and other relevant texts.

4. TREATMENT OF CONDITIONS AND ILLNESSES ASSOCIATED WITH PSYCHOSIS USING GLUCOCORTICOID RECEPTOR ANTAGONISTS

Antiglucocorticoids, such as mifepristone, are formulated as pharmaceuticals to be used in the methods of the invention. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

a. Glucocorticoid Receptor Antagonists as Pharmaceutical Compositions

The GR antagonists used in the methods of the invention can be administered parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of psychosis, the general medical condition of each patient, the resulting preferred method of administration and the like. Details on techniques for formulation and administration are well described in the scientific and patent literature, see, for example, the latest edition of "Remington's Pharmaceutical Sciences" (Maack Publishing Co, Easton Pa.).

GR antagonist pharmaceutical formulations can be prepared according to any method known to the art for the manufacture of pharmaceuticals. Such drugs can contain sweetening agents, flavoring agents, coloring agents and preserving agents. Any GR antagonist formulation can be admixtured with nontoxic pharmaceutically acceptable excipients which are suitable for manufacture.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of GR antagonist compounds with a solid excipient, optionally grinding a resulting mixture, and processing the mixture of granules, after adding suitable additional compounds, if desired, to obtain tablets or dragee cores. Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR antagonist mixed with a filler or binders such as lactose or starches, lubricants such as talc or magnesium stearate, and, optionally, stabilizers: In soft capsules, the GR antagonist compounds may be dissolved or suspended in suitable liquids, such as fatty oils, liquid paraffin, or liquid polyethylene glycol with or without stabilizers.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylnethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid. As an example of an injectable oil vehicle, see Minto (1997) *J. Pharmacol. Exp. Ther.* 281:93–102.

Dispersible powders and granules of the invention suitable for preparation of an aqueous suspension by the addition of water can be formulated from a GR antagonist in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical formulations of the invention can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

The GR antagonist pharmaceutical formulations of the invention can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, such as a solution of 1,3-butanediol. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

They can also be administered by in intranasal, intraocular, intravaginal, and intrarectal routes including suppositories, insufflation, powders and aerosol formulations (for examples of steroid inhalants, see Rohatagi (1995) *J. Clin. Pharmacol.* 35:1187–1193; Tjwa (1995) *Ann. Allergy Asthma Immunol.* 75:107–111).

Products of the invention which are preferably administered by the topical route can be administered as applicator sticks, solutions, suspensions, ,gels, creams, ointments, pastes, jellies, paints, powders, and aerosols. The GR antagonists of the invention, such as mifepristone, can be delivered by transdermally or via intradernal injection of drug (mifepristone)-containing microspheres, which slowly release subcutaneously (see Rao (1995) *J. Biomater Sci. Polym. Ed.* 7:623–645; for biodegradable and injectable gel formulations see Gao (1995) *Pharm. Res.* 12:857–863 (1995); for use of microspheres for oral administration, see Eyles (1997) *J. Pharm. Pharmacol.* 49:669–674). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5, that is combined with buffer prior to use.

In another embodiment, the GR antagonist formulations of the invention are useful for parenteral administration, such as intravenous administration or administration into a body cavity or lumen of an organ. The formulations for administration will commonly comprise a solution of the mifepristone dissolved in a pharmaceutically acceptable carrier, preferably an aqueous carrier. A variety of aqueous carriers can be used, e.g., buffered saline and the like. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of GR antagonist in these formulations can vary widely, and will be selected primarily based on fluid volumes, viscosities, body weight and the like in accordance with the particular mode of administration selected and the patient's needs.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. See Al-Muhammed (1996) *J. Microencapsul.* 13:293–306; Ostro (1989) *Am. J. Hosp. Pharm.* 46:1576–1587.

b. Determining Dosing Regimens for Glucocorticoid Receptor Antagonists

The methods of the invention ameliorate psychosis, i.e., prevent, slow the onset of, decrease the frequency of, diminish the severity of or cure a psychosis and/or its complications. The amount of GR antagonist adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen must also take into consideration the pharmacokinetics, i.e., the GR antagonists' rate of absorption, bioavailability, metabolism, clearance, and the like (see, for example, Hidalgo-Aragones (1996) *J. Steroid Biochem. Mol. Biol.* 58:611–617; Groning (1996) Pharmazie 51:337–341; Fotherby (1996) Contraception 54:59–69; Johnson (1995) *J. Pharm. Sci.* 84:1144–1146; Rohatagi (1995) *Pharmazie* 50:610–613; Brophy (1983) *Eur. J. Clin. Pharmacol.* 24:103–108; the latest Remington's, supra). In one study, less than 0.5% of the daily dose of mifepristone was excreted in the urine; the drug bound extensively to circulating albumin (see Kawai (1989) supra).

The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of mifepristone formulations may be administered depending on the dosage and frequency as required and tolerated by the patient. The formulations should provide a sufficient quantity of mifepristone to effectively ameliorate the psychosis. Thus, a typical pharmaceutical formulations for oral administration of mifepristone would be about 8 to 20 mg/kg of body weight per patient per day. Dosages from about 2 mg to about 30mg per kg of body weight per patient per day may be used, particularly when the drug is administered to an anatomically secluded site, such as the cerebral spinal fluid (CSF) space, in contrast to administration orally, into the blood stream, into a body cavity or into a lumen of an organ. Substantially higher dosages are possible in topical administration. Actual methods for preparing parenterally administrable GR antagonist formulations will be known or apparent to those skilled in the art and are described in more detail in such publications as *Remington's Pharnaceutical Science*, 15th ed., Maack Publishing Company, Easton, Pa. (1980). In a preferred embodiment of the invention, the invention provide for a method of treating psychosis by administering mifepristone in a daily amount of about 8 to 12 mg per kilogram of body weight per day. Using this dosage, the administration can continue for a period of about four days. Alternatively, in another embodiment the mifepristone is administered in a daily amount of about 600 mg per day. See also Nieman, In "Receptor Mediated Antisteroid Action," Agarwal, et al., eds., De Gruyter, New York (1987).

After a pharmaceutical comprising a GR antagonist of the invention has been formulated in a acceptable carrier, it can be placed in an appropriate container and labeled for treatment of an indicated condition. For administration of GR antagonists, such labeling would include, for example, instructions concerning the amount, frequency and method of administration. In one embodiment, the invention provides for a kit for the amelioration of psychosis in a human which includes a glucocorticoid receptor antagonist and instructional material teaching the indications, dosage and schedule of administration of the glucocorticoid receptor antagonist. When mifepristone is the GR antagonist used, the instructional material indicates that the GR antagonist can be used for in a daily amount of about 8 to 12 mg per kilogram of body weight per day, and, the administration of the glucocorticoid receptor antagonist continues for period of about four days.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Treating Psychotic Major Depression with Mifepristone

The following example details studies which demonstrate that the method of the invention is an effective treatment for psychosis.

Study Background

This study demonstrates that a glucocorticoid receptor antagonist, mifepristone, administered in dosages of about 10 mg per kg per day over a relatively short treatment period, is an effective treatment for psychotic major depression. The basic strategy was to demonstrate that high dose mifepristone, in the range of 600 mg per day, over a relatively short period of time—about four days—is an effective treatment for psychotic major depression. The study requires a nine day, closely observed hospital stay.

Patient Selection

Individuals included in this study were diagnosed as psychotic depressives using criteria as set forth by the DSM-IV, as described above. This diagnosis was confumed by two psychiatrists. All are between the ages of 18 and 75.

Apart from hypercortisolemia, they have no major medical problems. They have no signs of Cushings Syndrome. No children of childbearing potential are included in the study. Individuals admitting to having used illicit drugs within a month prior to admission for the study are excluded. Individuals admitting to drinking in excess of two ounces of alcohol daily are excluded from the study. No anti-psychotic medication was taken within three days of entering the study. While, concurrent anti-depressant was not a criteria used to excluded anyone from the study, no individual was started on an anti-depressant medication while participating in the study. All patients gave their written consent to a protocol approved by the Human Subjects Committee at Stanford University Medical Center.

All participants were given the Hamilton Rating Scale for Depression (HAM-D, Hamilton (1962) *J. Neurol. Psychiatry*, supra, discussed above) and the Structured Clinical Interview for DSM-IV Axis I mood disorders tests (as described above). Only individuals with a score greater than 21 on the HAM-D test continued in the study (a HAM-D score of >21 indicates moderate to severe depression). The HAIM-D Rating Scale was also given after administration of mifepris tone, as described below.

On the basis of these criteria, sixteen (16) individuals with psychotic major depression were selected.

Measuring Blood Cortisol Levels

The "Double Antibody Cortisol Kit™" (Diagnostic Products Corporation, Los Angeles, Calif.) was used to measure blood cortisol levels. This test is a competitive radioimmunoassay in which $^{125}$I-labeled cortisol competes with cortisol from an clinical sample for antibody sites, and was performed essentially according to manufacturer's instructions using reagents supplied by manufacturer.

Briefly, blood was collected by venipuncture and serum separated from the cells. The samples were stored at 2 to 8° C. for up to seven days, or up to two month frozen at −20° C. Before the assay, samples were allowed to come up to room temperature (15–28° C.) by gentle swirling or inversion. Sixteen tubes in duplicate at 25 microliters of serum per tube was prepared. Cortisol concentrations were calculated from the prepared calibration tubes. Net counts equaled the average CPM minus the average non-specific CPM. Cortisol concentrations for the unknowns were estimated by interpolation from the calibration curve (Dudley, et al. (1985) *Clin. Chem.* 31:1264–1271).

Assessing Amelioration of Psychosis

Formal psychiatric assessment, including the HAM-D rating scale (Overall (1962) supra; Kaplan (1995), supra, discussed above), the Brief Psychiatric Rating Scale (BPRS) (Overall (1962) supra; Kaplan (1995), supra, discussed above) and the Clinical Global Impression (GAF) evaluation (DSM-IV, supra, pages 30 to 31; Kaplan, ed. (1995), supra) was carried out on days one, three, five, seven and nine of the study at 10:00 AM (at 1000 hours). A paragraph recall test (see below) was given at 11:30 AM (at 1130 hours) on days one, five and nine. Cortisol levels were measured serially every half hour from 1:30 to 4:00 PM (1300 to 1600 hours) on days one, five and nine. Plasma ACTH and Plasma HVA was measured serially every hour from 1300 to 1600 on days one, five and nine. Routine biological and hematological studies were conducted daily, particularly to screen for evidence of relative adrenal insufficiency, i.e., hypoglycemia, eosinophilia.

One means used to assess/measure improvement, or amelioration of psychosis in the study was the "Wallach Recognition Test" (a paragraph recall test). Newly evaluated individuals with an initial diagnosis of psychotic major depression, diagnosed as described above, were given a recognition task adapted from Wallach (1980) supra. Subjects listened to a taped recording of a sixteen-word list presented at the rate of one word every ten seconds. The subject repeats each of the sixteen words and is asked to think of what the words mean to them. Following the presentation of the list, the subject engages in a twenty minute motor distraction task. The subject then listens to a fifty-word list containing the sixteen original target words plus thirty-four background distraction words. The subject then is asked to discern between target words and distractors.

Dosage Regimen and Administration of Mifepristone

Sixteen newly admitted patients with an admitting diagnosis of psychotic major depression confirmed by two psychiatrists were enrolled in the study. Each patient conformed with all of the above described criteria. The subject is given either: 600 milligrams of mifepristone per day orally, in one dose, over four days, followed by four days of placebo; or, four days of placebo followed by the same dose and regimen of mifepristone (patients serving as their own control in this "cross-over" study). In the patients administered mifepristone, three two hundred milligram tablets per day were given for four days. The mifepristone (RU486) tablets were supplied by The Population Council and Roussel Uclaf, Hoechst Marion Roussel USA, Kansas City, Mo. The tablets were manufactured by Shanghai HuaLian Pharmaceuticals Co., Ltd., Shanghai, China (currently the sole commercial source of RU486).

Both patients and the investigators are "blind" as to which compound (test mifepristone or placebo) the patient received.

Results

The protocol has been competed for three patients. While the study is a double-blind placebo controlled study, and to date the blind has not been broken, two preliminary observations can be made. First, each subject receiving mifepristone as described above showed a significant improvement in their psychiatric condition. Second, no adverse effects were subjectively reported by the patient or objectively observed by raters or staff.

When the Wallach Recognition Test was used to measure the degree of amelioration of psychosis in the study's subjects, all individuals who received mifepristone showed an amelioration of their psychosis. On the average, the number of times test subjects perceived distracters as words they had actually heard before (in the test's tape recording) declined between 25% and 100% after treatment.

On the average HAM-D scores declined from about 26 to about 13.5. Brief Psychiatric Rating Scale (BPRS) scores declined from about 40.5 to about 29.5.

Clinical Global Impression (CGI scale, based on a GAF evaluation, discussed above, see DSM-IV, supra, pages 30 to 31; Kaplan, ed. (1995)) scores dropped from about 5 (indicating "markedly depressed") to about 3 ("mildly depressed"). As discussed above, the GAF scale is particularly useful in tracking the clinical progress of individuals in global terms using a single measure.

These data demonstrate that high dose mifepristone, in the range of 600 mg per day, over a relatively short period of time—about four days—is an effective and safe treatment for psychotic major depression.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of ameliorating psychosis in a patient in need thereof by administration of an amount of a glucocorticoid receptor antagonist effective to ameliorate the psychosis, with the proviso that the patient not be suffering from Cushing's Syndrome and the psychosis is associated with major depression.

2. The method of claim 1, wherein the glucocorticoid receptor antagonist comprises a steroidal skeleton with at least one phenyl-containing moiety in the 11-beta position of the steroidal skeleton.

3. The method of claim 2, wherein the phenyl-containing moiety in the 11-beta position of the steroidal skeleton is a dimethylaminophenyl moiety.

4. The method of claim 2, wherein the glucocorticoid receptor antagonist comprises mifepristone.

5. The method of claim 2, wherein the glucocorticoid receptor antagonist is selected from the group consisting of RU009 and RU044.

6. The method of claim 1, wherein the glucocorticoid receptor antagonist is administered in a daily amount of between about 8 to 20 mg per kilogram of body weight per day.

7. The method of claim 1, wherein the glucocorticoid receptor antagonist is administered in a daily amount of about 8 to 12 mg per kilogram of body weight per day.

8. The method of claim 1, wherein the glucocorticoid receptor antagonist is administered for about four days.

9. The method of claim 1, wherein the glucocorticoid receptor antagonist is administered in a daily amount of about 600 mg per day.

10. The method of claim 1, wherein the administration is once per day.

11. The method of claim 1, wherein the mode of administration is oral.

12. The method of claim 1, wherein the mode of administration is transdermal.

13. A method of ameliorating psychotic major depression in a patient in need thereof comprising administering to the patient mifepristone in a daily amount of about 8 to 12 mg per kilogram of body weight per day, wherein the administration continues for a period of about 4 days, with the proviso that the patient is not suffering from Cushing's Syndrome.

* * * * *

UNITED STATES PATENT AND TRADEMARK OFFICE
CERTIFICATE OF CORRECTION

PATENT NO.   : 6,150,349
DATED        : November 21, 2000
INVENTOR(S)  : Schatzberg et al.

It is certified that error appears in the above-identified patent and that said Letters Patent is hereby corrected as shown below:

Column 1,
Line 4, please enter:

--   STATEMENT REGARDING FEDERALLY SPONSORED RESEARCH
        This invention was made with goverment support under contract no. 5T32MH awarded by the National Institutes of Health. The government may have certain rights in this invention. --

Signed and Sealed this

Fifteenth Day of April, 2003

JAMES E. ROGAN
*Director of the United States Patent and Trademark Office*